United States Patent
Griffith

(10) Patent No.: US 6,974,570 B1
(45) Date of Patent: Dec. 13, 2005

(54) SHAVING LOTION KIT AND METHOD OF PREPARING SKIN AND UNWANTED HAIR FOR SHAVING

(76) Inventor: Dana K. Griffith, 3809 Virginia Ave., Charleston, WV (US) 25304

( * ) Notice: Subject to any disclaimer, the term of this patent is extended or adjusted under 35 U.S.C. 154(b) by 226 days.

(21) Appl. No.: 10/285,596

(22) Filed: Oct. 30, 2002

(51) Int. Cl.$^7$ ............................ A61K 7/15; A61K 7/00
(52) U.S. Cl. ........................................ 424/73; 424/401
(58) Field of Search ................................ 424/73, 401

(56) References Cited

Primary Examiner—Shengjun Wang

(57) ABSTRACT

Shaving lotion kits and methods of preparing skin and unwanted hair for shaving prepare skin and unwanted hair for shaving without requiring cleanup. This is critical when water, soap, or towels are unavailable. The user can conveniently shave any area of the body, even when water is not accessible, such as when resting in a hospital bed or while camping. The shaving lotion kit also creates less mess than dispensing shaving cream from a can into the hand. Shaving lotion that is not removed during the shaving process can simply be rubbed into the skin. Unlike shaving creams, the shaving lotion also has vitamins and sunscreen to protect the skin and promote skin health.

8 Claims, 2 Drawing Sheets

18 — INGREDIENTS:
- WATER
- GLYCERIN
- SUNFLOWER OIL
- VITAMIN A
- CORN OIL
- GLYCERYL STEARATE
- TITANIUM DIOXIDE
- DISODIUM EDTA
- UREA
- LECITHIN
- RETINYL PALMITATE
- CAPRYLOYL COLLAGEN AMINO ACIDS
- CETYL PHOSPHATE
- SILVER MAGNESIUM ALUMINUM PHOSPHATE
- ISOBUTANE
- TOCOPHERYL ACETATE
- C11-13 ISOPARAFFIN
- DMDM HYDANTOIN
- SOYA STEROL
- STEARAMIDE AMP
- TRIETHANOLAMINE
- ALOE VERA GEL
- FRAGRANCE
- POLYSORBATE 80NF
- POLYSORBATE 20NF
- METHYLCELLULOSE
- OCTYL METHOXYCINNAMATE
- BENZOPHENONE 3
- SODIUM LAURYL SULFATE
- TRETINOIN
- CITRIC ACID (MONOHYDRATE)
- MINERAL OIL
- QUATERNIUM-15

18 — INGREDIENTS
- WATER
- GLYCERIN
- SUNFLOWER OIL
- VITAMIN A
- CORN OIL
- GLYCERYL STEARATE
- TITANIUM DIOXIDE
- DISODIUM EDTA
- UREA
- LECITHIN
- RETINYL PALMITATE
- CAPRYLOYL COLLAGEN AMINO ACIDS
- CETYL PHOSPHATE
- SILVER MAGNESIUM ALUMINUM PHOSPHATE
- ISOBUTANE
- TOCOPHERYL ACETATE
- C11-13 ISOPARAFFIN
- DMDM HYDANTOIN
- SOYA STEROL
- STEARAMIDE AMP
- TRIETHANOLAMINE
- ALOE VERA GEL
- FRAGRANCE
- POLYSORBATE 80NF
- POLYSORBATE 20NF
- METHYLCELLULOSE
- OCTYL METHOXYCINNAMATE
- BENZOPHENONE 3
- SODIUM LAURYL SULFATE
- TRETINOIN
- CITRIC ACID (MONOHYDRATE)
- MINERAL OIL
- QUATERNIUM-15

FIG.1

SHAVING LOTION KIT AND METHOD OF PREPARING SKIN AND UNWANTED HAIR FOR SHAVING

BACKGROUND OF THE INVENTION

1. Field of the Invention

The present invention relates to a shaving lotion kit and method of preparing skin and unwanted hair for shaving for use in connection with unwanted hair removal. The shaving lotion kit and method of preparing skin and unwanted hair for shaving has particular utility in connection with shaving when shaving cream, water, soap, or a towel are not available.

2. Description of the Prior Art

Shaving lotion kits and methods of preparing skin and unwanted hair for shaving are desirable for preparing skin and unwanted hair for shaving without requiring cleanup. This is critical when water, soap, or towels are unavailable. The user can conveniently shave any area of the body, even when water is not accessible, such as when resting in a hospital bed or while camping. The shaving lotion kit also creates less mess than dispensing shaving cream from a can into the hand. Shaving lotion which is not removed during the shaving process can simply be rubbed into the skin. Unlike shaving creams, the shaving lotion also has vitamins and sunscreen to protect the skin and promote skin health.

The use of skin care kits is known in the prior art. For example, U.S. Pat. No. 6,013,270 to Hargraves et al. discloses a skin care kit. However, the Hargraves et al. '270 patent does not have a tray with a removable lid, and has further drawbacks of not providing a method of preparing skin and unwanted hair for shaving.

U.S. Pat. No. 6,042,815 to Kellner et al. discloses a water and oil emulsion solid cosmetic composition that moisturizes skin. However, the Kellner et al. '815 patent does not have a tray with a removable lid, and additionally does not provide a method of preparing skin and unwanted hair for shaving.

Similarly, U.S. Pat. No. 6,086,903 to Trinh et al. discloses personal treatment compositions and/or cosmetic compositions containing enduring perfume that provide a lasting olfactory sensation. However, the Trinh et al. '903 patent does not have a tray with a removable lid, and also does not provide a method of preparing skin and unwanted hair for shaving.

In addition, U.S. Pat. No. 6,074,652 to Ishiwatari et al. discloses an oil-in-water emulsified composition and oil-in-water emulsifying agent that displays excellent emulsion stability and feeling of use. However, the Ishiwatari et al. '652 patent does not have a tray with a removable lid, and has further drawbacks of not providing a method of preparing skin and unwanted hair for shaving.

Furthermore, U.S. Pat. No. 6,008,246 to Ito et al. discloses an external preparation for skin containing a low-molecular-weight betaine that moisturizes skin. However, the Ito et al. '246 patent does not have a tray with a removable lid, and does not provide a method of preparing skin and unwanted hair for shaving.

Lastly, U.S. Pat. No. 6,017,549 to Knight et al. discloses non-irritating cosmetic and pharmaceutical compositions that decrease irritation on the skin caused by an irritating active agent in a topical cosmetic or pharmaceutical emulsion. However, the Knight et al. '549 patent does not have a tray with a removable lid, and has the additional deficiency of lacking a method of preparing skin and unwanted hair for shaving.

While the above-described devices fulfill their respective, particular objectives and requirements, the aforementioned patents do not describe a shaving lotion kit and method of preparing skin and unwanted hair for shaving that allows shaving when shaving cream, water, soap, or a towel are not available. The above patents make no provision for a tray with a removable lid. They also do not have a method of preparing skin and unwanted hair for shaving.

Therefore, a need exists for a new and improved shaving lotion kit and method of preparing skin and unwanted hair for shaving that can be used for shaving when shaving cream, water, soap, or a towel are not available. In this regard, the present invention substantially fulfills this need. In this respect, the shaving lotion kit and method of preparing skin and unwanted hair for shaving according to the present invention substantially departs from the conventional concepts and designs of the prior art, and in doing so provides an apparatus primarily developed for the purpose of shaving when shaving cream, water, soap, or a towel are not available.

SUMMARY OF THE INVENTION

In view of the foregoing disadvantages inherent in the known types of skin care kits now present in the prior art, the present invention provides an improved shaving lotion kit and method of preparing skin and unwanted hair for shaving, and overcomes the above-mentioned disadvantages and drawbacks of the prior art. As such, the general purpose of the present invention, which will be described subsequently in greater detail, is to provide a new and improved shaving lotion kit and method of preparing skin and unwanted hair for shaving which has all the advantages of the prior art mentioned heretofore and many novel features that result in a shaving lotion kit and method of preparing skin and unwanted hair for shaving which is not anticipated, rendered obvious, suggested, or even implied by the prior art, either alone or in any combination thereof.

To attain this, the present invention essentially comprises a hollow shaving lotion packet containing a towelette impregnated with a shaving lotion composition. The present invention also comprises a method of preparing skin and unwanted hair for shaving which comprises the step of applying an effective amount of a shaving lotion composition to at least one part of the human body.

There has thus been outlined, rather broadly, the more important features of the invention in order that the detailed description thereof that follows may be better understood and in order that the present contribution to the art may be better appreciated.

The invention may also include a tray with a removable lid comprising the hollow shaving lotion packet. Alternatively, the shaving lotion packet could be formed by adhering the outer edges of two sheets together, thereby resulting in a hollow center between the sheets.

The following Examples further describe and demonstrate current embodiments of the shaving lotion composition within the scope of the present invention. The Examples are given solely for the purpose of illustration and are not be construed as limitations of the present invention as many variations thereof are possible without departing from its spirit and scope. All percentages, ratios, and parts herein, in the Specification, Examples, and claims, are by weight and are approximations, unless otherwise stated.

| Ingredients | Example A | Example B | Example C | Example D |
|---|---|---|---|---|
| Water/Glycerin | 20% | 31% | 21% | 23% |
| Sunflower oil | 15% | 15% | 15% | 15% |
| Vitamin A | 10% | 0% | 10% | 10% |
| Corn oil | 3% | 3% | 3% | 3% |
| Glyceryl stearate | 4% | 4% | 4% | 4% |
| Titanium dioxide | 1% | 1% | 1% | 0% |
| Disodium EDTA | 1% | 1% | 1% | 1% |
| Urea | 1% | 1% | 1% | 1% |
| Lecithin | 1% | 1% | 1% | 1% |
| Retinyl palmitate | 1% | 1% | 1% | 1% |
| Capryloyl collagen amino acids | 2% | 2% | 2% | 2% |
| Cetyl phosphate | 1% | 1% | 1% | 1% |
| Silver magnesium aluminum phosphate | 1% | 1% | 1% | 1% |
| Isobutane | 1% | 1% | 1% | 1% |
| Tocopherol acetate | 1% | 0% | 1% | 1% |
| C11–13 isoparaffin | 1% | 1% | 1% | 1% |
| DMDM hydantoin | 1% | 1% | 1% | 1% |
| Soya sterol | 1% | 1% | 1% | 1% |
| Stearamide AMP | 1% | 1% | 1% | 1% |
| Triethanolamine | 2% | 2% | 2% | 2% |
| Aloe vera gel | 2% | 2% | 2% | 2% |
| Fragrance | 1% | 1% | 0% | 1% |
| Polysorbate 80NF | 2% | 2% | 2% | 2% |
| Polysorbate 20NF | 2% | 2% | 2% | 2% |
| Methylcellulose | 2% | 2% | 2% | 2% |
| Octyl methoxycinnamate | 1% | 1% | 1% | 0% |
| Benzophenone 3 | 1% | 1% | 1% | 0% |
| Sodium lauryl sulfate | 1% | 1% | 1% | 1% |
| Tretinoin | 1% | 1% | 1% | 1% |
| Citric acid (monohydrate) | 1% | 1% | 1% | 1% |
| Mineral oil | 15% | 15% | 15% | 15% |
| Quaternium-15 | 2% | 2% | 2% | 2% |

There are, of course, additional features of the invention that will be described hereinafter and which will form the subject matter of the claims attached.

Numerous objects, features and advantages of the present invention will be readily apparent to those of ordinary skill in the art upon a reading of the following detailed description of presently current, but nonetheless illustrative, embodiments of the present invention when taken in conjunction with the accompanying drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved shaving lotion kit and method of preparing skin and unwanted hair for shaving that has all of the advantages of the prior art skin care kits and none of the disadvantages.

It is another object of the present invention to provide a new and improved shaving lotion kit and method of preparing skin and unwanted hair for shaving that may be easily and efficiently manufactured and marketed.

An even further object of the present invention is to provide a new and improved shaving lotion kit and method of preparing skin and unwanted hair for shaving that has a low cost of manufacture with regard to both materials and labor, and which accordingly is then susceptible of low prices of sale to the consuming public, thereby making such shaving lotion kit and method of preparing skin and unwanted hair for shaving economically available to the buying public.

Still another object of the present invention is to provide a new shaving lotion kit and method of preparing skin and unwanted hair for shaving that provides in the apparatuses and methods of the prior art some of the advantages thereof, while simultaneously overcoming some of the disadvantages normally associated therewith.

Even still another object of the present invention is to provide a shaving lotion kit and method of preparing skin and unwanted hair for shaving for shaving when shaving cream, water, soap, or a towel are not available. This allows the user to shave without the use of shaving cream.

Still yet another object of the present invention is to provide a shaving lotion kit and method of preparing skin and unwanted hair for shaving for shaving when shaving cream, water, soap, or a towel are not available. This makes it possible to rub any remaining shaving lotion into the skin.

An additional object of the present invention is to provide a shaving lotion kit and method of preparing skin and unwanted hair for shaving for shaving when shaving cream, water, soap, or a towel are not available. This eliminates the need to wash the shaved area after shaving.

A further object of the present invention is to provide a shaving lotion kit and method of preparing skin and unwanted hair for shaving for shaving when shaving cream, water, soap, or a towel are not available. This promotes skin health.

A still further object of the present invention is to provide a shaving lotion kit and method of preparing skin and unwanted hair for shaving for shaving when shaving cream, water, soap, or a towel are not available. This protects the skin from sunburn.

Lastly, it is an object of the present invention to provide a new and improved shaving lotion kit and method of preparing skin and unwanted hair for shaving for shaving when shaving cream, water, soap, or a towel are not available.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated current embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is an ingredient list of the current embodiment of the shaving lotion composition constructed in accordance with the principles of the present invention.

The same reference numerals refer to the same parts throughout the various figures.

DESCRIPTION OF THE CURRENT EMBODIMENT

Figure 2:
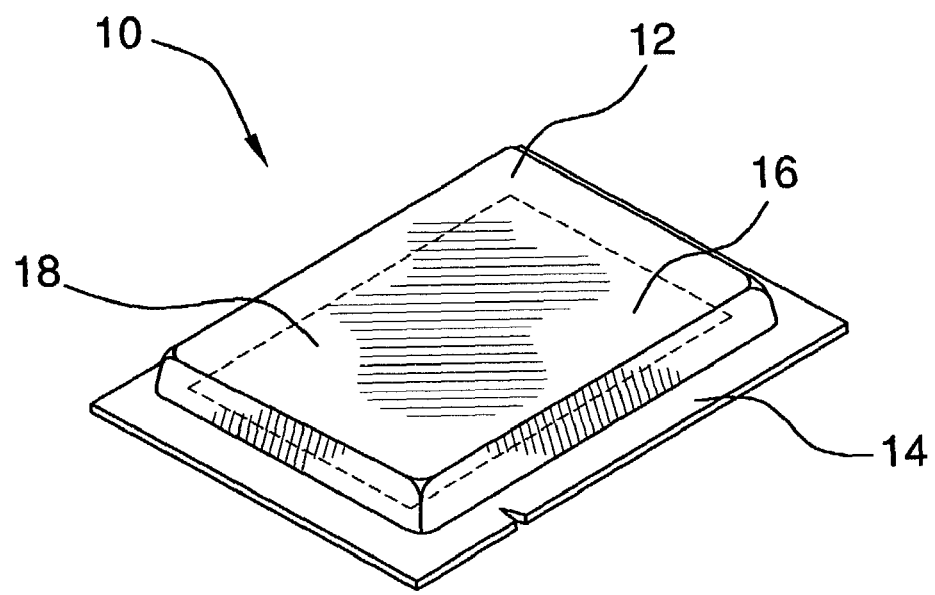
FIG. 2 is a bottom perspective view of the shaving lotion kit of the present invention.

Referring now to the drawings, and particularly to FIGS. 1–2, a current embodiment of the shaving lotion kit of the present invention is shown and generally designated by the reference numeral 10.

In FIG. 1, a new and improved shaving lotion composition 18 of the present invention for shaving when shaving cream, water, soap, or a towel are not available is illustrated and will be described. More particularly, the shaving lotion composition 18 consists of water, glycerin, and C11–13 isoparaffin acting as solvents. C11–13 isoparaffin is a mixture of hydrocarbons (mineral oils). Sunflower oil and corn oil are added as nonvolatile emollient oils. Capryloyl collagen amino acids are used as an antistatic agent Polysorbate 80 NF and polysorbate 20 NF are used as nonionic organic surfactants. Polyethylene sorbitan monooleate (Polysorbate 80) belongs to a general class of emulsifiers called Polyoxyetheylene Sorbitan Fatty Esters or Polysorbates. Polysorbate 20 (polyoxyethylene sorbitan monolaurate) is another common polysorbate. NF refers to the grade and indicates that the chemical meets the requirements of the National Formulary and is exceptionally high in purity. Particulate matter, in the form of methylcellulose and silver magnesium aluminum phosphate are surface treated with lecithin and mineral oil to render the particles more lipophilic in nature. Titanium dioxide is introduced as a sunscreen to physically block ultraviolet radiation. Chemical sunscreens are also employed, specifically benzophenone 3 and octyl methoxycinnamate. PH of the composition is modified by the addition of citric acid and triethanolamine. Vitamin A and tocopherol acetate (vitamin E) are added to enhance skin health. Aloe vera gel is included as a moisturizer. Fragrance is added to induce an olfactory response. Glyceryl stearate, urea, soya stenol, and cetyl phosphate are used as emulsifiers. Retinyl palmitate and tretinoin are used to promote skin regeneration. Disodium EDTA is employed as a chelating agent. Isobutane and quaternium-15 are used as preservatives. Sodium lauryl sulfate is added as a detergent. Stearamide AMP is used for viscosity control.

In FIG. 2, a new and improved shaving lotion kit 10 of the present invention for shaving when shaving cream, water, soap, or a towel are not available is illustrated and will be described. More particularly, the shaving lotion kit 10 consists of a tray 12 which is made of plastic in the current embodiment of the present invention. The tray must be impermeable to shaving lotion composition 18 contained within it so that shaving lotion composition 18 cannot escape. Removably attached to the top of tray 12 is lid 14 made of foil which must also be impermeable to shaving lotion composition 18 to prevent leaks. Lid 14 is attached to the top of tray 12 by an adhesive. Contained within tray 12 is towelette 16 made of a nonwoven cloth capable of absorbing shaving lotion composition 18. Shaving lotion composition 18 impregnates towelette 16.

In use, it can now be understood that the user peels off lid 14 from tray 12 to expose towelette 16. Towelette 16, impregnated with shaving lotion composition 18, is rubbed on the skin and unwanted hair to be shaved. Once the shaving process is complete, any remaining shaving lotion composition 18 can simply be rubbed into the skin; no washing to remove shaving lotion composition 18 is required.

While a current embodiment of the shaving lotion kit and method of preparing skin and unwanted hair for shaving has been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention. For example, any suitable sunscreen substance such as zinc oxide or PABA, may be used instead of the titanium dioxide, benzophenone 3, and octyl methoxycinnamate described. Also, the sunflower oil and corn oil could be replaced by coconut oil, cottonseed oil, linseed oil, soybean oil, olive oil, palm oil, walnut oil, and the like. Furthermore, a wide variety of fragrances may be used depending on the olfactory response desired. Also, additional vitamins such as vitamin C could be added, and numerous alternative formulations of vitamins E and A could be employed.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A shaving lotion composition comprising:
   a water glycerin solution, wherein said water glycerin solution is in the amount of 20–35% by weight;
   oils, wherein said oils are in the amount of 33% by weight;
   vitamins, wherein said vitamins are in the amount of up to 11% by weight;
   glyceryl stearate, wherein said glyceryl stearate is in the amount of 4% by weight;
   ultraviolet radiation protective agent, wherein said ultraviolet radiation protective agent is in the amount of up to 3% by weight;
   disodium edta, wherein said disodium edta is in the amount of 1% by weight;
   urea, wherein said urea is in the amount of 1% by weight;
   lecithin, wherein said lecithin is in the amount of 1% by weight;
   retinyl palmitate, wherein said retinyl palmitate is in the amount of 1% by weight;
   capryloyl collagen amino acids, wherein said capryloyl collagen amino acids are in the amount of 2% by weight;
   cetyl phosphate, wherein said cetyl phosphate is in the amount of 1% by weight;
   silver magnesium aluminum phosphate, wherein said silver magnesium aluminum phosphate is in the amount of 1% by weight;
   isobutane, wherein said isobutane is in the amount of 1% by weight;
   C11–13 isoparaffin, wherein said C11–13 isoparaffin is in the amount of 1% by weight;

dmdm hydantoin, wherein said dmdm hydantoin is in the amount of 1% by weight;
soya sterol, wherein said soya sterol is in the amount of 1% by weight;
stearamide amp, wherein said stearamide amp is in the amount of 1% by weight;
triethanolamine, wherein said triethanolamine is in the amount of 2% by weight;
aloe vera gel, wherein said aloe vera gel is in the amount of up to 2% by weight;
fragrance, wherein said fragrance is in the amount of up to 1% by weight;
polysorbate 80 NF, wherein said polysorbate 80 NF is in the amount of 2% by weight;
polysorbate 20 NF, wherein said polysorbate 20 NF is in the amount of 2% by weight;
methylcellulose, wherein said methylcellulose is in the amount of 2% by weight;
sodium lauryl sulfate, wherein said sodium lauryl sulfate is in the amount of 1% by weight;
tretinoin, wherein said tretinoin is in the amount of 1% by weight;
citric acid monohydrate, wherein said citric acid monohydrate is in the amount of 1% by weight; and
quaternium-15, wherein said quaternium-15 is in the amount of 2% by weight.

2. The shaving lotion composition as defined in claim 1, wherein said oils are at least one of the group consisting of mineral oil, sunflower oil, and corn oil.

3. The shaving lotion composition as defined in claim 1, wherein said vitamins are at least one of the group consisting of vitamin A, vitamin C, and vitamin E.

4. The shaving lotion composition as defined in claim 1, wherein said ultraviolet radiation protective agent is at least one of the group consisting of titanium dioxide, zinc oxide, PABA, octyl methoxycinnamate, and benzophenone 3.

5. A method of preparing skin and unwanted hair for shaving, which comprises the step of applying a composition to the skin and unwanted hair comprising:
a water glycerin solution, wherein said water glycerin solution is in the amount of 20–35% by weight;
oils, wherein said oils are in the amount of 33% by weight;
vitamins, wherein said vitamins are in the amount of up to 11% by weight;
glyceryl stearate, wherein said glyceryl stearate is in the amount of 4% by weight;
ultraviolet radiation protective agent, wherein said ultraviolet radiation protective agent is in the amount of up to 3% by weight;
disodium edta, wherein said disodium edta is in the amount of 1% by weight;
urea, wherein said urea is in the amount of 1% by weight;
lecithin, wherein said lecithin is in the amount of 1% by weight;
retinyl palmitate, wherein said retinyl palmitate is in the amount of 1% by weight;
capryloyl collagen amino acids, wherein said capryloyl collagen amino acids are in the amount of 2% by weight;
cetyl phosphate, wherein said cetyl phosphate is in the amount of 1% by weight;
silver magnesium aluminum phosphate, wherein said silver magnesium aluminum phosphate is in the amount of 1% by weight;
isobutane, wherein said isobutane is in the amount of 1% by weight;
C11–13 isoparaffin, wherein said C11–13 isoparaffin is in the amount of 1% by weight;
dmdm hydantoin, wherein said dmdm hydantoin is in the amount of 1% by weight;
soya sterol, wherein said soya sterol is in the amount of 1% by weight;
stearamide amp, wherein said stearamide amp is in the amount of 1% by weight;
triethanolamine, wherein said triethanolamine is in the amount of 2% by weight;
aloe vera gel, wherein said aloe vera gel is in the amount of up to 2% by weight;
fragrance, wherein said fragrance is in the amount of up to 1% by weight;
polysorbate 80 NF, wherein said polysorbate 80 NF is in the amount of 2% by weight;
polysorbate 20 NF, wherein said polysorbate 20 NF is in the amount of 2% by weight;
methylcellulose, wherein said methylcellulose is in the amount of 2% by weight;
sodium lauryl sulfate, wherein said sodium lauryl sulfate is in the amount of 1% by weight;
tretinoin, wherein said tretinoin is in the amount of 1% by weight;
citric acid monohydrate, wherein said citric acid monohydrate is in the amount of 1% by weight; and
quaternium-15, wherein said quaternium-15 is in the amount of 2% by weight.

6. The shaving lotion composition as defined in claim 5, wherein said oils are at least one of the group consisting of mineral oil, sunflower oil, and corn oil.

7. The shaving lotion composition as defined in claim 5, wherein said vitamins are at least one of the group consisting of vitamin A, vitamin C, and vitamin E.

8. The shaving lotion composition as defined in claim 5, wherein said ultraviolet radiation protective agent is at least one of the group consisting of titanium dioxide, zinc oxide, PABA, octyl methoxycinnamate, and benzophenone 3.

* * * * *